United States Patent [19]

Dillon

[11] 4,040,930
[45] Aug. 9, 1977

[54] OXYGEN SENSOR

[75] Inventor: James E. Dillon, Elgin, Ill.

[73] Assignee: UOP Inc., Des Plaines, Ill.

[21] Appl. No.: 655,662

[22] Filed: Feb. 5, 1976

[51] Int. Cl.² ............................................. G01N 27/46
[52] U.S. Cl. ................................................ 204/195 S
[58] Field of Search ............................ 204/1 S, 195 S

[56] References Cited

U.S. PATENT DOCUMENTS

| | | | |
|---|---|---|---|
| 3,768,259 | 10/1973 | Carnahan et al. | 204/195 S |
| 3,835,012 | 9/1974 | Hemak | 204/195 S |
| 3,844,920 | 10/1974 | Burgett et al. | 204/195 S |
| 3,847,778 | 11/1974 | Riddel | 204/195 S |
| 3,909,385 | 9/1975 | Spielberg et al. | 204/195 S |
| 3,915,828 | 10/1975 | Cleary et al. | 204/195 S |
| 3,928,161 | 12/1975 | McIntyre et al. | 204/195 S |
| 3,940,327 | 2/1976 | Wagner et al. | 204/195 S |
| 3,960,692 | 6/1976 | Weyl et al. | 204/195 S |
| 3,960,693 | 6/1976 | Weyl et al. | 204/195 S |

Primary Examiner—T. Tung

Attorney, Agent, or Firm—James R. Hoatson, Jr.; Barry L. Clark; William H. Page, II

[57] ABSTRACT

Oxygen sensor for automotive use incorporates a disc of solid electrolyte material which is mounted in the end of a short ceramic tube so as to be positioned near the end of a metal body member in which the tube is mounted and adjacent to the wall of an exhaust pipe into which the body member is mounted. For improved stability against vibration damage, the ceramic tube has an unsupported length which is less than about 150% of its diameter. Precious metal stripes on the ceramic tube carry the electrical signal generated between the electrodes on the hot electrolyte to relatively cool portions of the body member where they are conducted to external terminals through spring biased contacts. A tubular metal shield, which may enclose a porous ceramic filter, protects the electrolyte from exhaust particles and directs heat from the center of the exhaust pipe to the electrolyte disc.

7 Claims, 3 Drawing Figures

U.S. Patent  Aug. 9, 1977  4,040,930
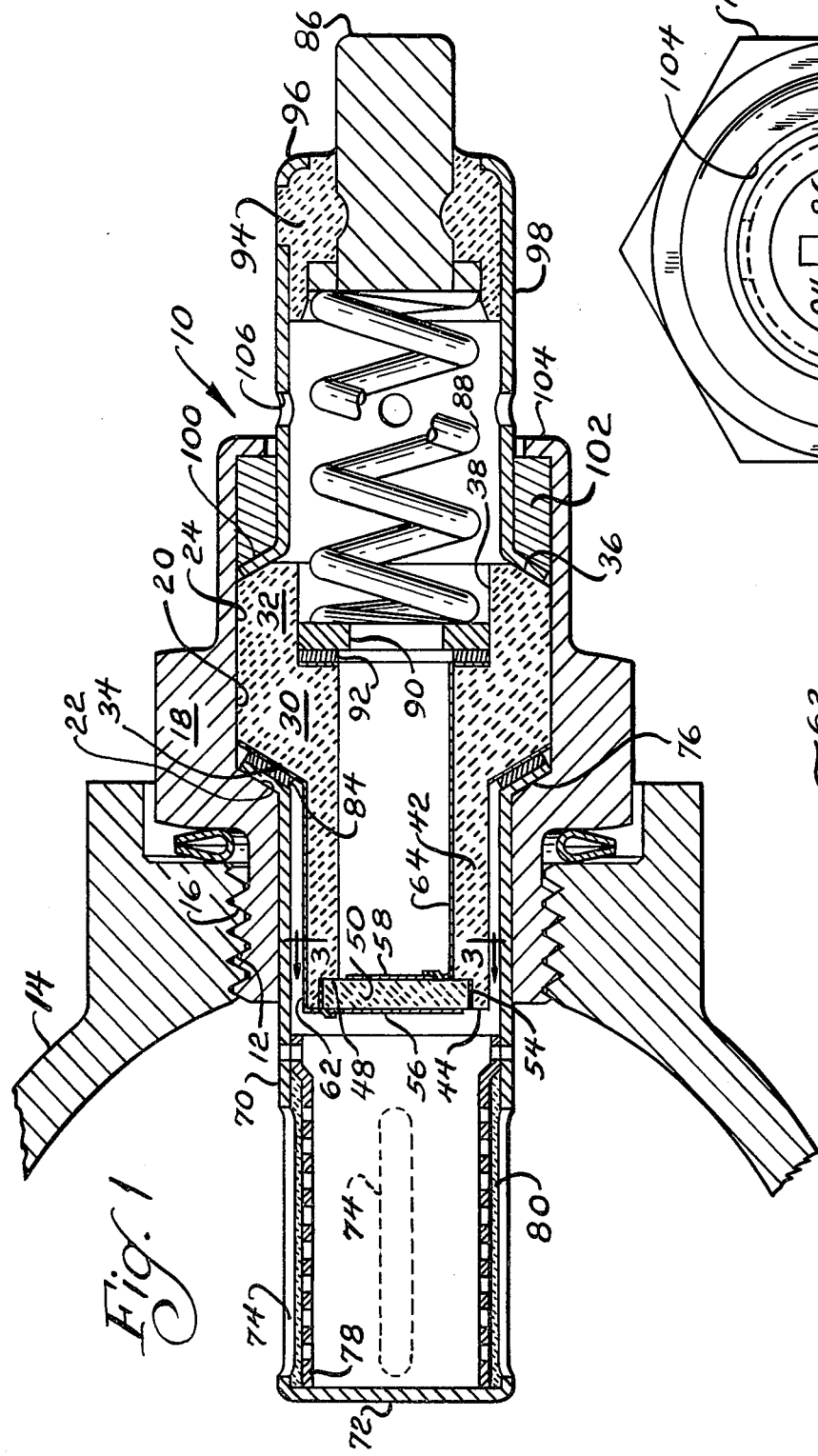
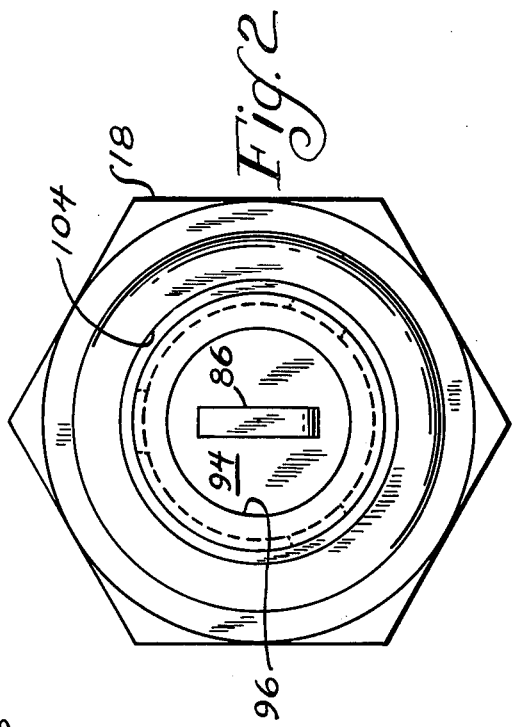
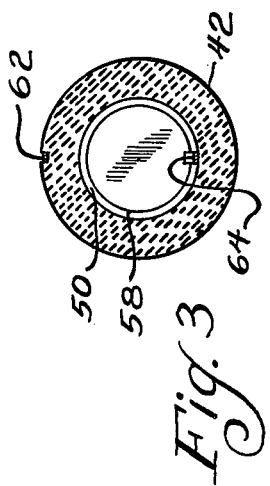

OXYGEN SENSOR

BACKGROUND OF THE INVENTION

The invention relates to oxygen sensors for generating a low voltage signal in response to differences in oxygen partial pressures on opposite sides of a solid electrolyte cell such as zirconia stabilized with yttria. In automotive applications where temperatures in the exhaust stream are generally sufficiently high to meet the approximately 425° C. minimum desirable requirements of a zirconia sensing cell, it has been conventional practice to locate the zirconia cell near the center of the exhaust stream where the temperature usually runs approximately 535° C. Where the sensing cell has been made in the form of a disc mounted in a metal tube, problems of sealing the disc against gas leakage have been encountered due to differences in the temperature coefficient of expansion. Other workers in this field have proposed utilizing zirconia in closed end, elongated thimble form to permit sealing to be accomplished at the cool end of the thimble where differential expansion is inconsequential. Such elongated thimbles are, however, quite expensive and fragile.

SUMMARY OF THE INVENTION

It is among the objects of the present invention to provide an oxygen sensor which is easy to manufacture, economical to produce, and has a long life expectancy in the rugged environment of an automotive exhaust system. These and other objects are attained by the sensor of the present invention wherein the stabilized zirconia electrolyte is in the form of a small wafer or disc which is mounted in a recess at one end of a molded, generally tubular ceramic body. Since zirconia is a ceramic material, the problem of providing a seal between the wafer and ceramic tube is quite simple compared to the problem of sealing a ceramic wafer to a metal tube. For example, a glass frit seal is quite satisfactory. Where a metal tube is used, dimensional changes caused by the considerably different temperature coefficients of expansion of metal and ceramic make it extremely difficult to produce a seal which will provide the required hermetic seal for long periods of time. To increase the ability of the ceramic tube to withstand vibration and the hostile environment of an exhaust system, the ceramic tube is made to be quite short. Preferably, the tube has a cantilevered portion which supports the electrolyte wafer at its free end and has a length less than 150% of its diameter. The ceramic tube is mounted in a metal body and is held in place by means of an enlarged diameter portion at the end of the tube opposite the wafer end. Preferably, the cantilevered portion of the ceramic tube is positioned inside the metal body member and spaced radially inwardly from the walls thereof.

A thin metal shield member extends axially outwardly from the metal body member so that when the sensor is mounted in an exhaust pipe the shield member will extend to about the center of the exhaust system. The metal shield has a closed outer end and elongated openings in its sides. The openings permit the exhaust gases to enter and leave the interior of the shield member wherein they contact the outer electrode coated surface of the electrolyte wafer. Preferably, a thick, paper-like layer of ceramic fibers is positioned in contact with the interior of the shield member to filter out particles in the exhaust stream which could erode away or otherwise damage the electrode surface. An internal perforated screen member which is attached to the shield member provides internal support for the layer of ceramic fibers. The outer end and the walls of the metal shield member serve to radiate and conduct the high heat at the center of the exhaust stream to the electrolyte wafer. Leads for the electrode surfaces on either side of the electrolyte preferably comprise narrow platinum stripes which extend along the inner and outer walls of the ceramic tube to rearwardly positioned conductive gaskets. The stripes can be painted on in liquid form or, they can be attached in solid form such as foil, to the ceramic tube when it is molded.

BRIEF DESCRIPTION OF THE DRAWINGS

FIG. 1 is a side view in axial cross section showing the improved oxygen sensor in cooperation with an exhaust pipe;

FIG. 2 is an end view of the sensor shown in FIG. 1; and

FIG. 3 is a section view taken on line 3—3 of FIG. 1.

DESCRIPTION OF THE PREFERRED EMBODIMENT

The oxygen sensor indicated generally at 10 is adapted to be placed into a threaded bushing member 12 which is either integrally formed with or attached to a combustion engine exhaust pipe 14. The bushing 12 is engaged by threads 16 formed on one end of the sensor's metal body or housing 18. Internally of the housing 18, a recess 20 is defined by an angled wall or shoulder portion 22 and a side wall 24. Positioned within the recess 20 is a ceramic body 30 which may be made of Forstertite insulating material. The ceramic body 30 has an enlarged diameter portion 32 and angled front and rear portions 34, 36 which fit within the recess 20 and cooperate with portions of it to rigidly retain the ceramic body 30. The ceramic body 30 has a recess 38 formed in its outer end for a purpose to be hereinafter described. The opposite end of the ceramic body 30 comprises a tubular end portion 42 which is spaced from the inner walls of the metal body 18 and supported in a cantilever fashion relative to the angled front wall portion 34. The end face 44 of the end portion 42 contains a recess 48 into which a solid electrolyte wafer or disc 50 of a material such as yttria stabilized zirconia is hermetically sealed. The seal may take the form of a layer of glass frit 54 which is fired at about 1010° C., or about 65° above its melting point, to the body 30 and the electrolyte 50. Alternatively, the electrolyte could be embedded in the ceramic body 30 during molding of the body or shrunk fit within the body as the body 30 is fired. The sensing electrode 56 is preferably made of a catalytic material such as porous platinum and is affixed to the inner end of the electrolyte 50 while a reference electrode 58, also preferably platinum, is affixed to the outer or reference side of the electrolyte. A lead member such as a platinum stripe 62 contacts the sensing electrode 56 and traverses the length of the tubular portin 42 to its termination on the angled wall portion 34. The inner lead member 64 comprises a platinum stripe which contacts the reference electrode 58 and traverses the inner wall of the tubular portion 42 and terminates at the inner wall portion of the recess 38. The outer lead member 62 is preferably located within a shallow groove formed on the outer wall of the end portion 42 so as to protect it during assembly of the ceramic body 30 to the housing 18. The inner stripe 64 can be conveniently applied by a painting process. Preferably, the lead stripes 62, 64 are applied in a liquid state and are fired to the body member 30 at a high temperature.

A tubular metal shield member 70 having a closed end 72 and exhaust gas inlet slots 74 projects into the exhaust stream and is held within the metal body 18 by means of a flange portion 76 which contacts the angled shoulder 22. To prevent particles in the exhaust stream from damaging the electrode 56, the shield 70 is preferably provided with an inner perforated sleeve portion 78 which cooperates with the outer wall of the sleeve to capture a layer of ceramic fiber filter material 80.

Electrical contact between the sensing electrode 56 and the housing 18 is provided by placing a conductive gasket 84 of a material such as that sold under the trademark Grafoil between the remote end of lead member 62 and the flange 76 formed on shield 70 which contacts angled shoulder 22. The reference lead member 64 is connected to an outer electrical terminal member 86 by means of a metal spring 88, a metal washer 90 and a conductive gasket 92. The terminal 86 is molded into a molded insulator portion 94 which is retained against outward movement by flange portions 96 of a terminal housing member 98. The terminal housing 98 has an angled flange 100 at its inner end which contacts angled surface 36 on the ceramic body 30 and is retained by metal ring member 102 and a flange portion 104 on the outer end of body 18. Since the spring 88 is separated from the hot electrolyte 50 by the length of the ceramic body 30 and is exposed to cooling air which can enter the unit through apertures 106, it will retain its temper and apply sufficient force to the ceramic body 30 to maintain firm electrical contact between the lead members 62, 64 and the respective conductive gaskets 84, 92.

I claim as my invention:

1. An oxygen sensor for use in an automotive exhaust stream comprising a metal housing having a shouldered recess portion intermediate its ends, fastening means on the inner end of said metal housing adapted to cooperate with complementary fastening means on the side wall of an exhaust member containing gases to be sensed, a hollow, generally tubular, ceramic insulating body positioned within said metal housing and having an enlarged diameter shoulder portion intermediate its ends which is restrained against forward movement toward said inner end of said metal housing by said shouldered recess portion, the forward portion of said insulating body being unsupported and radially spaced from the inner wall of said metal housing, a solid electrolyte member of a material different from the ceramic body sealed to said ceramic insulating body at the inner end thereof and having electrodes on the opposed sides thereof, the combined length of the forward portion of said insulating body and said solid electrolyte member being less than 150% of the outer diameter of said forward portion, said solid electrolyte member being positioned axially at about the inner end of said metal housing, a generally tubular, apertured metal shield member extending axially from said metal housing a sufficient distance that its inner end will be in or near the center of the exhaust stream when said sensor is mounted in the side wall of an exhaust conduit.

2. The oxygen sensor of claim 1 wherein a porous ceramic filter member is positioned inside said shield member.

3. The oxygen sensor of claim 2 wherein said shield member comprises inner and outer radially spaced apertured wall portions, said filter member being positioned in the space between said wall portions.

4. The oxygen sensor of claim 1 wherein said hollow ceramic insulating body has stripe-like metallic coatings on the inner and outer surfaces of its forward portion in contact with the electrodes on said electrolyte.

5. The oxygen sensor of claim 4 wherein said metallic coatings are platinum.

6. The oxygen sensor of claim 4 wherein said coating on the outer surface is recessed.

7. The oxygen sensor of claim 4 wherein said metallic coatings are contacted by spring biassed conductive gaskets at the ends thereof which are remote from said electrolyte.

* * * * *